Figure 1:
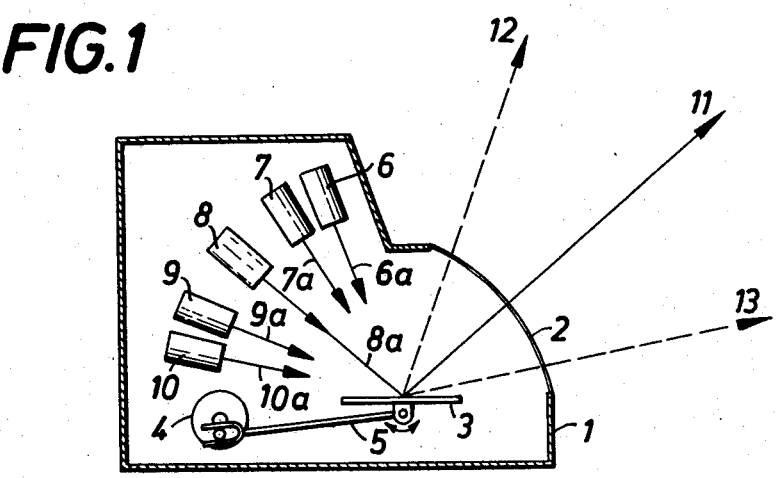

United States Patent [19]

Kretz

[11] 4,337,661
[45] Jul. 6, 1982

[54] EQUIPMENT FOR ULTRASONIC EXAMINATION

[75] Inventor: Carl Kretz, Zipf, Austria

[73] Assignee: Kretztechnik Gesellschaft m.b.H., Zipf, Austria

[21] Appl. No.: 74,162

[22] Filed: Sep. 10, 1979

[30] Foreign Application Priority Data

Jan. 23, 1979 [AT] Austria .................................. 464/79

[51] Int. Cl.³ ...................... G01N 29/00; A61B 10/00
[52] U.S. Cl. ........................................ 73/628; 128/663
[58] Field of Search ................. 73/626, 628, 620, 641; 128/663

[56] References Cited

U.S. PATENT DOCUMENTS

| | | | |
|---|---|---|---|
| 3,107,521 | 10/1963 | McClure | 73/640 |
| 3,403,671 | 10/1968 | Flaherty et al. | 128/660 |
| 3,693,414 | 9/1972 | Soldner | 73/641 X |
| 3,939,707 | 2/1976 | Kossoff | 128/663 X |
| 3,990,300 | 11/1976 | Kossoff | 73/621 X |
| 4,010,634 | 3/1977 | Baumgartner | 73/641 |
| 4,084,582 | 4/1978 | Nigam | 73/620 X |
| 4,102,204 | 7/1978 | Kretz | 73/626 |
| 4,163,394 | 8/1979 | Soldner | 73/626 |
| 4,185,501 | 1/1980 | Proudian | 73/641 |
| 4,204,435 | 5/1980 | Bridoux et al. | 73/626 |
| 4,208,916 | 6/1980 | Thomenius et al. | 73/626 |

FOREIGN PATENT DOCUMENTS

| | | | |
|---|---|---|---|
| 2643918 | 3/1978 | Fed. Rep. of Germany | 73/626 |
| 772083 | 4/1957 | United Kingdom | 73/626 |

*Primary Examiner*—Daniel M. Yasich
*Attorney, Agent, or Firm*—Kurt Kelman

[57] ABSTRACT

In an ultrasonic scanner, a plurality of sound transducers are operable to project sound beams defining spaced sound paths into a sectional plane of an object and to receive echoes therefrom. The sound paths may be oscillatingly swept in the sectional plane during operating cycles so that the sound path of each sound transducer coincides at least once during each oscillating cycle with a predetermined line of reflection in the sectional plane. A fluorescent screen receives some of the echo signals to display them in a section scan mode while a sound transducer control operates each sound transducer when none of the sound paths coincides with the predetermined line in each given cycle. A scan mode control operates when the sound path coincides with the predetermined line for displaying the section scan mode in response to the echo signals in a different scan mode several times per cycle.

8 Claims, 4 Drawing Figures

EQUIPMENT FOR ULTRASONIC EXAMINATION

This invention relates to equipment for ultrasonic examination by means of the pulse-echo method, comprising a section-scanning and display system with which a sound beam is movable by driven elements in a preselected sectional plane and a section display derived from the resulting echo signals is traced on a fluorescent screen, and an accessory for displaying certain signals derived from the sectional plane in a different mode, particularly as a time-motion display or A-scan display.

The information obtained in examinations using the pulse-echo method can be indicated in various ways. In the A-scan display, the echoes received are displayed as pips, the spacing of which corresponds to the interval of time between their arrivals and is a measure of the relative position of the reflecting points where the echoes have originated. The height of the pip is a measure of the intensity of the echo and of the magnitude and reflectance of the reflecting surfaces. In the section image method, the intensity of the echo is used to modulate the tracing beam which is moved across the fluorescent screen in analogy to the sound beam which scans the sectional plane in the object. If the sound beam is moved in a section plane, a B-scan display will be obtained, which is mainly used at present. If the section plane is at right angles to the sound beam and in most cases parallel to the surface of the object being scanned then a C-scan display will be obtained. In the so-called time-motion method, a curve is traced which represents the movement of a reflecting surface as a function of time.

None of the methods which have been outlined can furnish in itself an information which is so complete that the other methods are no longer required. For instance, in an examination of the heart, a section display of the heart can be traced and, if the picture frequency is sufficiently high, even a moving section display can be traced, whereas depths and distances can be measured in an A-scan display and the time-motion method may be used for a recording of motions, particularly of the cardiac valves, in the form of a curve, which is called an ultrasonic cardiogram (UCG). This permits an exact quantitative evaluation and an examination during a plurality of cardiac periods so that irregular motions can easily be detected.

A known equipment is simply provided with means for effecting a change over so that displays in different modes can be traced in succession. This affords the advantage that many of the components of an ultrasonic equipment can be used for all modes of display. A section-scanning mechanism comprising a sound transducer which can be arrested may be provided, or a section-scanning mechanism which can be replaced by a simple sound transducer for an A-scan examination or a time-motion examination, as well as change-over switches for setting the equipment for the desired mode of display. Because in that case the examinations using displays in different modes are always made in succession, the relationships between the examinations are not always definite and particularly in medical examinations there is no perfect assurance that the results obtained are actually the results of examinations of the same region of the body.

Based on the recognition that simultaneous displays in the several scan modes or a display of rapidly changing scan modes will furnish more information than separate consecutive displays, equipment has been disclosed in U.S. Pat. No. 4,010,634 and in which a moving section display is traced as well as a target line which can be adjusted in the section display as desired. Switching means suppress a display of signals on said arget line and cause said signals to be displayed in at least one different mode. In that known equipment, a display of such signals in the A-scan mode is mainly contemplated because only the signals which would be displayed on the target line become available for a display is a different mode during a complete scan of the sectional plane by the sound beam. In case of a usual picture frequency of 10 to 20 pictures per sound, this means that a line is traced only 20 to 40 times so that only a corresponding number of signals are available for the different mode. The number of such signals is sufficient for an A-scan display of steady-state conditions but is insufficient for a satisfactory display of relatively fast motions by the time-motion method. Whereas an accessory may be used by which the sound transducer moved to scan the sectional plane is stopped in response to a separate switching signal when the target line has been reached so that a series of signals become available in the target line position, a stopping for a time which would be sufficient for a time-motion display will decrease the contrast of the section image so that only a rapid alternation between the two modes of display is possible rather than a continuous simultaneous observation of the two modes. Practice has shown that at least 100 to 200 scanning line signals per second would be required for a clear and definite time-motion image.

It may also be mentioned that a sound beam which is adjustable by mechanically driven elements for the generation of a section display can be produced by a driven sound transducer, in which case the sound beam is introduced virtually directly into the object being examined if the sound transducer oscillates about an axis which is disposed on the surface of the object or is disposed outside of and parallel to said surface, or if the sound beam is introduced indirectly from a sound transducer which is disposed in front of a parabolic reflector and driven to rotate. Alternatively, the sound beam can be indirectly introduced in an arrangement comprising a moving reflector and a sound transducer which is stationary or is also moved by the drive means.

It is an object of the invention to provide ultrasonic equipment which is of the kind described in the U.S. patent and which can display the results of ultrasonic examination in different modes at the same time, which modes of display include also the display of a moving section image and a time-motion display.

This object is accomplished with a plurality of sound transducers, which define respective sound paths projected on a common sectional plane wherein they extend spaced apart and preferably diverging, each of said sound transducers being operable to project a sound beam along the sound path defined by said sound transducers by a scanning mechanism operable to cyclically reciprocate said sound paths in said sectional plane so that each of said sound paths coincides with a predetermined line in said sectional plane at least once during each cycle of motion, and each sound transducer is adapted to be operated to generate signals for said different mode of display when the sound path defined by said sound transducer coincides with said predetermined line.

If the cycle time is so long that each sound transducer head is moved beyond the position in which the sound path defined by it coincides with the predetermined line, the sound path defined by each sound transducer will coincide with the predetermined line also during the return movement, so that a second series of signals from each sound transducer is available for the display in the different mode during each cycle of motion. On principle, each sound transducer can be switched for the display in the different mode when the sound path defined by the sound transducer coincides with the predetermined line. Alternatively, one, two or more sound transducers may be used only for the section display and the remaining sound transducers may be used for the time-motion display or a display in another mode. Switch means may be provided which cause displays in different modes, such as A-scan displays and time-motion displays, to be derived from the signals obtained during the "passage through zero" or which cause these signals to be displayed in alternation in the different modes. If additional circuitry is provided, it will be possible, in principle, particularly with divergent sound paths, to project non-interferring sound beams simultaneously from different sound transducers. If two or more sound transducers are used to generate the section display, each sound transducer may scan only a sector-shaped portion of the sectional plane so that a movement of each sound beam through a relatively small angle will be sufficient.

According to a preferred feature, the spacing of the sound transducers used to generate the signals for the display in the different mode depends on the motion of the sound paths defined by said sound transducers in the sectional plane so that said sound paths coincide with the predetermined line at equal intervals of time and the signals for the display in the different mode are also generated at equal intervals of time. In most cases, only one or two of the sound transducers will be used for the section display and, if desired, for the display in the different mode and the remaining sound transducers will be used only for the display in the different mode. Changeover switches may be provided, which disable the sound transducer or transducers for the section display when the sound path defined by any of the other sound transducers coincides with the predetermined line and which operate each of said other sound transducers when the sound path defined by it coincides with said line. In such an arrangement, only one sound transducer is operated at a time and only one signal-processing device is required for the equipment, provided that such device can be switched from one mode of display to the other. This can be effected by means of the above-mentioned change-over switch or a separate change-over switch. Theoretically, a double-beam cathode ray tube may be used which comprises separate deflecting means for each beam so that the two beams are used for respective modes of display. Alternatively, a normal cathode ray tube may be used together with the above-mentioned change-over switch if the latter is used to change over the deflecting means so that pictures of at least two modes of display can be traced. If the change-over frequency is sufficiently high, these images will be traced almost simultaneously and will be visible simultaneously owing to the persistence of the fluorescent screen and the slow response of the human eye.

The change over may be controlled in that the mechanism for moving the sound transducers controls a program generator for controlling the change-over switch or switches in dependence on the position of said mechanism.

In a preferred embodiment, the sound transducers are arranged in the scanning mechanism so that the sound paths defined by them are directed toward a reflector, which is adapted to be driven so as to oscillate to cause the sound beam or beams to scan the section plane.

Further details and advantages of the invention will become apparent from the following descriptions of the accompanying drawings.

In the accompanying drawings, the subject matter of the invention is shown by way of example.

Figure 2:
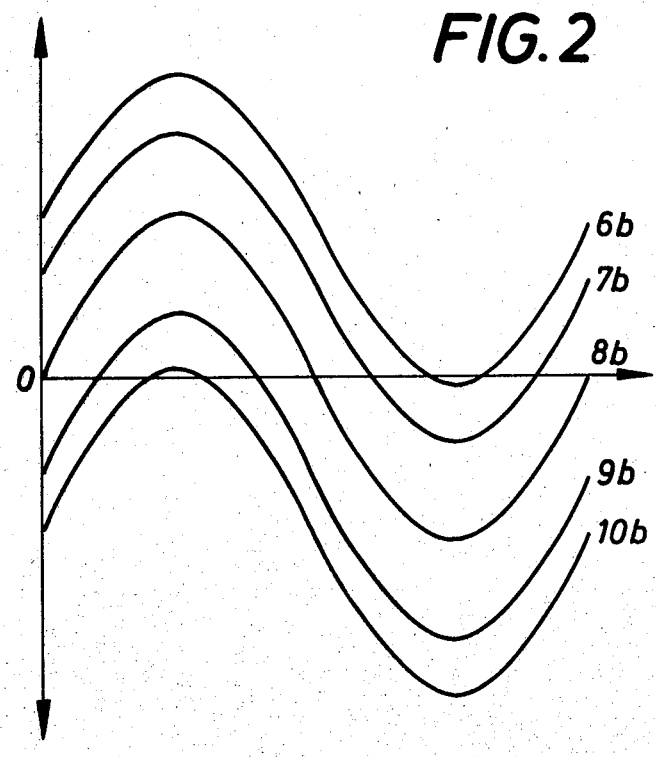
Figure 3:
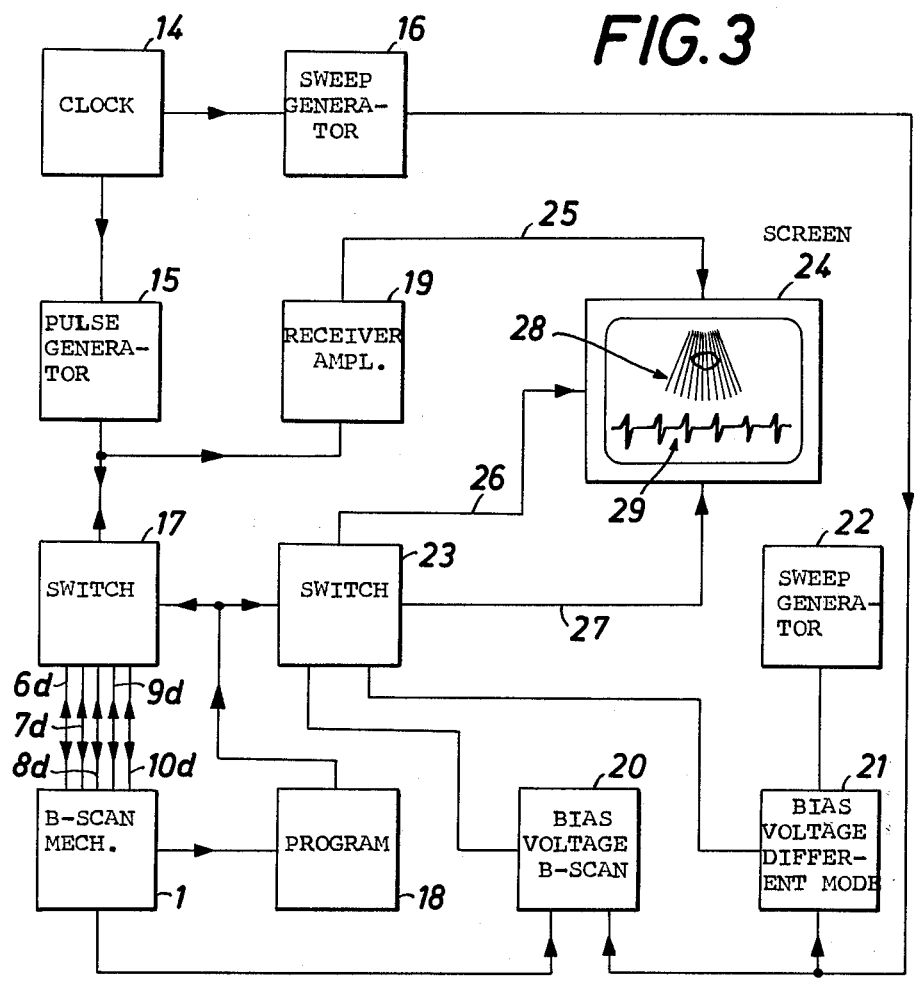
Figure 4:
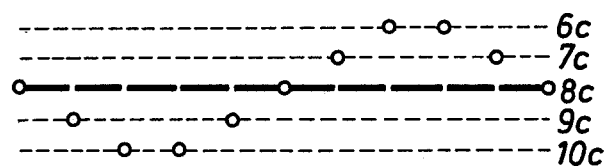

FIG. 1 is a highly diagrammatic view showing a scanning mechanism for use in equipment according to the invention, FIG. 2 represents the angular positions assumed by the sound paths defined by the several sound transducers under the control of the scanning mechanism in dependence on time, FIG. 3 is a block circuit diagram of the equipment and FIG. 4 is a schedule of the times at which the several sound transducers are switched.

A scanning mechanism as shown in FIG. 1 comprises a housing 1, which is filled with liquid and on one side has a sound-transmitting window 2. The window consists preferably of a flexible diaphragm. The housing 1 may communicate with an expansion vessel for receiving surplus liquid in case of a temperature rise or when the diaphragm 2 has been displaced into the housing. The housing contains a reflector 3, which can be oscillated by a crank drive 4, 5. The reflector should have a much higher reflectance for sound waves than the surrounding liquid. The reflector may consist of a metal mirror. An almost total reflection will be obtained if the front face of the reflector consists of a thin layer which has a rear surface in contact with air. In that case an air-filled hollow body is used, which is closed by the layer that forms the reflecting surface. The expression "thin layer" describes a layer which has a thickness that is much smaller than the wave length of the actually employed ultrasonic sound in said layer.

Five stationary sound transducers 6, 7, 8, 9, 10 are disposed in housing 1 and define sound paths 6a to 10a, which converge toward the center point or center line of the reflector. Sound beams projected by the sound transducer heads 6 to 10 along said sound paths are reflected by the reflector and the reflected sound beams diverge if the sound transducers were operated simultaneously.

In the present embodiment, the sound beam projected by the sound transducer 8 is used for the section display and when the reflector 3 is in the position shown is reflected by the reflector along a line 11 predetermined by the law of reflection. The pivotal movement of the reflector causes the beam to perform an angular movement between the extreme positions indicated by lines 12 and 13. During each oscillating cycle, the reflector 3 is moved through an angle which is one-half the angle between the lines 12 and 13 shown on the drawing. The reflector can be driven under particularly desirable conditions because it constitutes only a small moving mass and has a small amplitude of motion.

Alternatively, the sound transducers 6 to 10 may be arranged in the position of the reflector and may be driven to oscillate through an angle corresponding to the entire angular movement of the sound paths. In that case the sound path defined by the middle sound transducer 8 will again move between the lines 12 and 13. In such an arrangement, the sound transducers may slide on the diaphragm 2 and in that case are arranged to define divergent sound paths. In another alternative, the sound transducers may be arranged to define parallel sound paths and may be driven to reciprocate at right angles to the sound paths, i.e., in the longitudinal direction of the row of sound transducers. Whether a reflector is used and oscillated or whether the sound transducers themselves are driven through oscillating cycles, the sound paths defined by each sound transducer are oscillatingly swept in the sectional plane so that each path will coincide at least once during each cycle of oscillation with predetermined line 11.

The motion represented in FIG. 2 will be obtained regardless of the manner in which the motion is effected. Curves 6b to 10b represent the angular ranges scanned by the sound paths 6a to 10a, whether the sound paths enter the object directly or after having been reflected. The spacing of the sound transducers is selected so that curves 6b to 10b fulfill the following conditions: The center angle line of curve 8b associated with the middle sound path is intersected by each axis at least twice. (That center angle line corresponds to line 11 in FIG. 11.) The distances between the points at which the curves 6b to 10b cross the center angle line (passages through zero) are equal. If each of the sound transducers 6 to 10 is operated to project a sound beam and to receive the associated echoes for the display in the different mode whenever the scanning mechanism is in a position corresponding to the passage of said sound path through zero, elements of information for the display in the different mode will be obtained at a rate which is equal to twice the frequency of oscillation times the number of sound transducers. That rate can be increased by an increase of the number of sound transducers. The section display may be generated by more than one sound transducer. For instance, the sound transducers 7 and 9 may be operated in alternation to scan the sectional plane in the object. Equal intervals of time between the passages through zero will be obtained if the sound transducers 6 to 10 are properly arranged and their spacing is properly selected. FIG. 2 has been drawn on the assumption that the pivotal movement is a sine function. If the pivotal movement is performed in accordance with another function, the relative positions of the sound transducers will have to be altered.

The following explanations are based on the assumption that the sound beam projected by the sound transducer 8 is used for the section display and for the display in the different mode and that each of the sound transducers 6, 7 and 9, 10 are operated for the display in the different mode only when the sound path defined by the sound transducer passes through zero. The block circuit diagram shown in FIG. 3 represents a standard equipment, which is used for the pulse-echo method and is suitable for a section display and a display in at least one different mode, particularly for a time-motion display. Such equipment has been supplemented by two electronic change-over switches 17 and 23, which are controlled by the scanning mechanism. The sound transducer control operates each sound transducer when none of the sound paths defined by the plurality of sound transducers coincides with the predetermined line of reflection in each given cycle, and the scan mode control is operable when the sound path coincides with the predetermined line for displaying the section scan mode in response to the echo signals from the sound transducer in a different scan mode in a plurality of times per cycle when none of the sound paths defined by the plurality of sound transducers coincides with the predetermined line.

A clock 14 controls a pulse generator 15 and a sweep generator 16, which serves also as a line frequency generator for a time-motion display. The pulses generated by the pulse generator 15 are delivered to a change-over switch 17, which distributes them via leads 6d to 10d to respective sound transducers 6 to 10 in the scanning mechanism 1. The selection of the sound transducer to which a pulse that has been generated is to be delivered is effected by a program generator 18, which is controlled by the scanning mechanism 1, e.g., by a sensor (not shown) mounted on the axis of the reflector 3, in dependence on the instantaneous relative position of the reflector or in dependence on the position of the sound paths defined by the sound transducers. As a result, each sound transducer is operated only when the sound path defined by it assumes a certain position in an object. The echo signals, i.e., the signals derived from the echoes received by a sound transducer which is operated, are delivered by the change-over switch 17 to a receiver 19, in which they are processed for use as brightness control signals delivered via lead 25. The term "processing" includes amplifying, demodulating, filtering, threshold control, depth compensation etc.

For the section display, the electron beam is deflected onto a predetermined portion of the fluorescent screen 24 under control of a deflecting voltage generator 20, which generates the deflecting signals in dependence on the sawtooth voltage generated by the sweep generator 16 and on a position information delivered by the scanning mechanism 1, and under the control of a predetermined bias voltage, which defines the location of the display on the fluorescent screen. A different bias voltage is used for the display in the different mode so that the displays in the two modes appearing on the fluorescent screen 24 are disposed one over the other or one beside the other. In the present embodiment, the displays comprise a section display 28 and a time-motion display 29, such as UCG. A second deflecting voltage generator 21 is provided for the display in the different mode and generates the deflecting signals in dependence on the sawtooth voltage generated by the sweep generator 16 and of a second sweep generator 22, which effects the display. The two deflecting voltage generators 20 and 21 are connected to the deflecting system of the cathode ray tube 24 by leads 26, 27 and a change-over switch 23, which is also controlled by the program generator 18. The brightness control and deflecting signals may be directly delivered to the cathode ray tube or may be delivered to a memory device and may be read from the latter in an entirely different sequence, so that, e.g., a television monitor may be used as a display unit. This is not of basic significance for the function of the equipment.

FIG. 4 shows the timing of the operation of the switches 17 and 23 in the simple embodiment shown. The horizontal lines 6c to 10c are associated with respective sound transducers. The solid line indicates that the sound transducer 8 for the section display is operated during most of the time. Small circles indicate auxiliary points, which correspond to the times at which each sound transducer is operated for the time-motion display as its sound path passes through zero.

It has already been mentioned that the number of sound transducers used in the equipment according to the invention may be larger or smaller than in the present embodiment. If more than one sound transducer is provided for the section display, each of these sound transducers may be used to scan only part of the sectional plane, or change-over switches may be provided, e.g., for an increase or decrease of the area which is scanned. It has also been mentioned that the display in the different mode may be an A-scan display, which may be traced instead of or jointly with the time-motion display. In the latter case, the same signals may be used for the time-motion display and for the A-scan display. These signals are processed in parallel channels for these two modes of display or, if signals are available in an adequate number, an arrangement may be preferred in which some of the signals available for the display in the different mode may be used only for the A-scan display. It is emphasized that much less signals are required for the A-scan display than for the time motion display.

What is claimed is:

1. Equipment for ultrasonic examination by the pulse-echo method, comprising
   (a) a plurality of spaced sound transducers spaced in a predetermined pattern, each sound transducer comprising a primary sound transducer and being operable to project a sound beam defining a sound path into a common sectional plane of an object to be examined, and to receive echoes originating in the sectional plane in response to the projected sound beams for deriving echo signals therefrom, the sound paths being spaced from each other in the sectional plane,
   (b) a scanning mechanism operable in cycles to sweep the sound paths in the sectional plane oscillatingly so that the sound path defined by the sound beam of each sound transducer coincides at least once during each cycle with a predetermined line of reflection in the sectional plane,
   (c) display screen means operable to receive a part of the echo signals to display them in a section scan mode,
   (d) sound transducer control means operable to operate said primary sound transducer for operating each sound transducer when none of the sound paths defined by said plurality of sound transducers coincides with the predetermined line in each given cycle, and
   (e) scan mode control means operable when the sound path coincides with the predetermined line for displaying said section scan mode in response to the echo signals from said primary sound transducer in a different scan mode in a plurality of times per cycle when none of the sound paths defined by said plurality of sound transducers coincides with said predetermined line.

2. Equipment as set forth in claim 1, comprising two of said primary sound transducers.

3. Equipment as set forth in claim 1, in which said plurality of sound transducers comprise said primary sound transducer and additional sound transducers.

4. Equipment as set forth in claim 3, in which said sound transducer control means comprise change-over switch means for operating each of said plurality of sound transducers when the sound path defined by it coincides with said predetermined line.

5. Equipment as set forth in claim 4, in which said sound transducer control means comprise a program generator for controlling said change-over switch means in response to the position of said scanning mechanism.

6. Equipment as set forth in claim 1, in which said sound transducer control means comprise change-over switch means for operating each of said sound transducers when the sound path defined by it coincides with said predetermined line and for operating said primary sound transducer when none of said sound paths coincides with said predetermined line.

7. Equipment as set forth in claim 6, in which
   said primary sound transducer means are provided in addition to said plurality of sound transducers and
   said change-over switch means are arranged to disable said primary sound transducer means when one of said sound paths coincides with said predetermined line.

8. Equipment as set forth in claim 6, in which said sound transducer control means comprise a program generator for controlling said change-over switch means in response to the position of said scanning mechanism.

* * * * *